United States Patent [19]

Buchanan

[11] Patent Number: 5,380,091
[45] Date of Patent: Jan. 10, 1995

[54] INDICATING DEVICE

[75] Inventor: Nigel Buchanan, Cupar, United Kingdom

[73] Assignee: Alba Tools Limited, Fife, United Kingdom

[21] Appl. No.: 239,855

[22] Filed: May 9, 1994

Related U.S. Application Data

[63] Continuation of Ser. No. 122,646, Sep. 17, 1993, which is a continuation of Ser. No. 768,853, Dec. 4, 1991, abandoned.

[30] Foreign Application Priority Data

Apr. 8, 1989 [GB] United Kingdom ............... 8907948

[51] Int. Cl.$^6$ .................................................. G01N 25/08
[52] U.S. Cl. .................................... 374/16; 374/25; 374/164; 73/61.76
[58] Field of Search .............. 73/61.3, 61.43, 61.76; 374/16, 21, 25, 27, 54, 164, 170, 179, 208

[56] References Cited

U.S. PATENT DOCUMENTS

| | | | |
|---|---|---|---|
| 2,599,276 | 6/1952 | Norman | 374/16 |
| 3,084,535 | 4/1963 | Mackey | 374/27 |
| 4,109,527 | 8/1978 | Goode, Jr. | 374/170 |
| 4,408,902 | 10/1983 | Peuker | 374/27 |
| 4,484,822 | 11/1984 | Hancock | 374/27 |
| 4,484,823 | 11/1984 | Peuker | 374/54 |
| 4,562,554 | 12/1985 | Stixrud et al. | 374/170 |
| 4,648,055 | 3/1987 | Ishizaka et al. | 374/170 |
| 4,718,776 | 1/1988 | Gilland et al. | 374/170 |
| 4,735,512 | 4/1988 | Suzuki | 374/170 |
| 4,958,937 | 9/1990 | Lohberg et al. | 374/16 |

FOREIGN PATENT DOCUMENTS

| | | | |
|---|---|---|---|
| 1-280244 | 11/1989 | Japan | 374/27 |
| 8704249 | 7/1987 | WIPO | 374/27 |

OTHER PUBLICATIONS

IBM Technical Disclosure Bulletin, vol. 13, No. 8, Jan. 1971, Float Type Boiling Point Sensor, N. G. Aakalu et al.

Primary Examiner—William A. Cuchlinski, Jr.
Assistant Examiner—G. Bradley Bennett
Attorney, Agent, or Firm—Sixbey, Friedman, Leedom & Ferguson

[57] ABSTRACT

A portable hand-held device (1) is provided for testing the boiling point of fluids, especially hydraulic fluid such as brake fluid. The device includes a probe (3) for immersion in fluid to be tested, in particular in a fluid reservoir, and the probe (3) comprises an inner casing (11) defining a housing (11A) for a semi-encapsulated portion of fluid and an outer sheath (7) defining a shroud surrounding the inner casing (11). A heater (5) and a temperature sensor (6) are present in the housing (11A), and apertures (10, 13) are provided to permit fluid flows to and from the housing (11A). The device senses the onset of the equilibrium reflux boiling temperature of the fluid in the housing (11A).

23 Claims, 4 Drawing Sheets

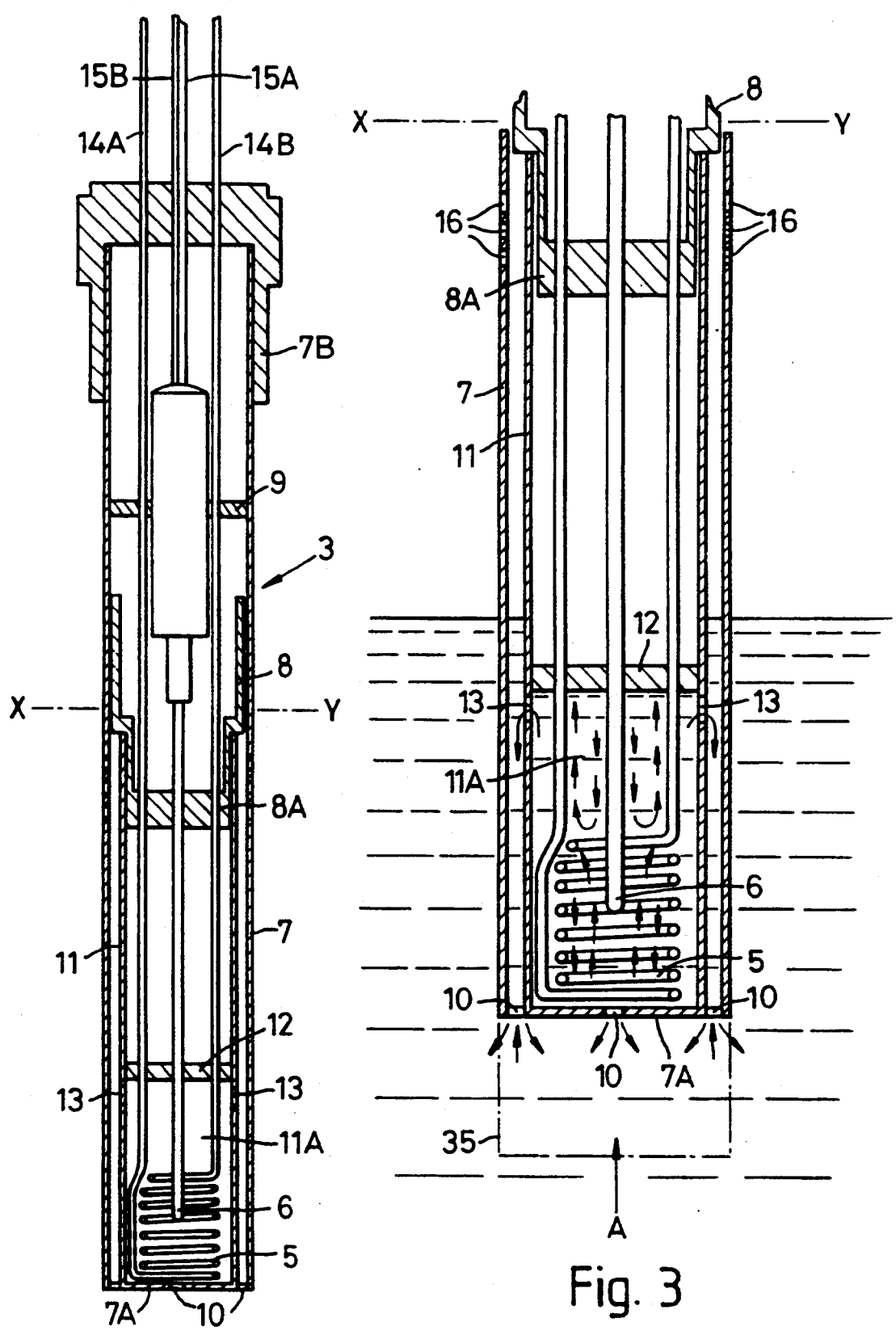

INDICATING DEVICE

This application is a continuation of Ser. No. 08/122,646 filed Sep. 17, 1993, which is a continuation of Ser. No. 07/768,853, filed Dec. 4, 1991, now abandoned.

DESCRIPTION

The present invention relates to an indicating device for indicating the boiling point of fluids, especially hygroscopic fluids such as hydraulic fluids, for example automotive brake and clutch fluid.

Brake fluid as used in the hydraulic braking systems of motor-cars and vans is hygroscopic; i.e. is capable of absorbing moisture, and this can have an adverse effect on braking performance, especially in the long term. In particular, the absorption of moisture in the brake fluid causes a lowering of the boiling point of the fluid and very possibly to such a degree that temperature increase in the braking system due for example to heavy braking or some fault condition can result in the brake fluid boiling and as will be appreciated this has a very deleterious effect on braking. Therefore it is beneficial to be aware of a serious lowering of the boiling point of brake fluid so that steps can be taken to change the faulty fluid.

A method and device for determining the boiling point of hygroscopic liquids, such as automotive brake and clutch fluid, is described and claimed in EP-A-0074415 (corresponding to U.S. Pat. No. 4,484,823). The method of EP-A-0074415 involves the heating of the liquid to be tested using a heater immersed in the liquid until the liquid evaporates and gas bubbles rise along the heater, the temperature of the heater effected by the gas bubbles being measured whence the boiling point of the liquid can be ascertained. A further pressure fluid boiling point testing device is described in GB-A-2139763, the device of GB-A-2139763 including a heater for fluid which also serves as a temperature sensor, the device relying on the formation of gas bubbles on the heater for a boiling point testing operation. These prior art devices have the disadvantage of not being particularly accurate and/or forming noxious vapours due to the evaporation of hydraulic fluid.

It is the principal object of the present invention to provide an indicating device for indicating the boiling point of brake fluid which avoids these disadvantages and which is convenient to operate but which gives accurate results.

According to the present invention there is provided an indicating device for indicating the boiling point of fluid especially a hygroscopic fluid such as hydraulic fluid comprising a meter preferably of the portable hand-held type including a probe portion for insertion into fluid in a fluid reservoir, heating means being provided in the probe portion for heating fluid in which the probe portion is immersed, said meter additionally including monitoring means for monitoring the temperature rise of fluid heated by said heating means so as to indicate the boiling point temperature of the fluid, characterised in that said probe includes a casing defining a housing wherein a portion of fluid to be tested is semi-encapsulated, the temperature monitoring means sensing the temperature of fluid in the housing heated by the heating means, and in that fluid inlet means are provided permitting fluid flows to and from the housing.

An embodiment of the present invention will now be described by way of example with reference to the accompanying drawings wherein:

FIG. 2 shows a cross-sectional elevation of the probe portion of the meter of FIG. 1;

FIG. 3 shows the lower part of the probe portion (i.e. below line X-Y) to a larger scale (and greater than actual size);

Figure 1:
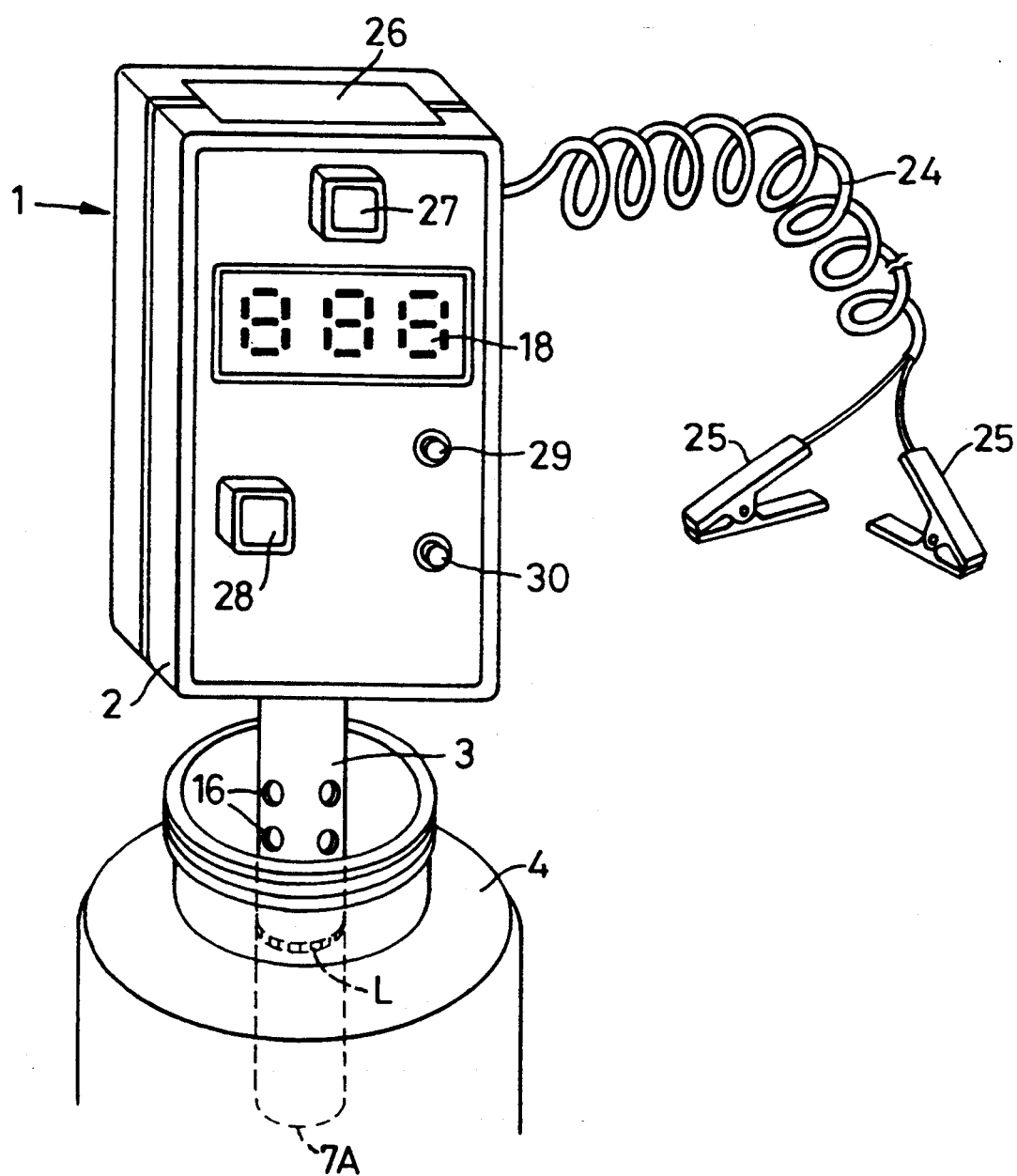
FIG. 1 shows a pictorial view of a fluid boiling point meter in accordance with the present invention, and especially intended for sensing the boiling point of automotive brake fluid.
Figure 4A:
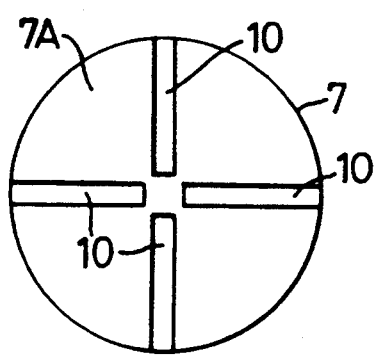
FIG. 4A shows a view in the direction of arrow A in FIG. 3, while 4B shows a similar view but for an alternative arrangement of the probe bottom.
Figure 4B:
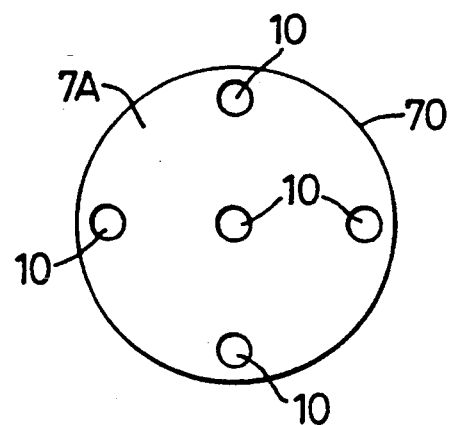
Figure 5:
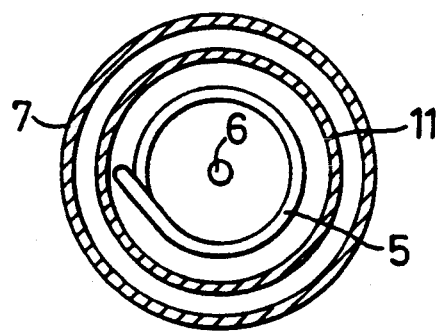
FIG. 5 shows a view in the direction of arrow A but with the probe bottom wall removed.

Referring to the drawings, a temperature indicating device or meter 1 for measuring the boiling point of automotive brake fluid comprises a main casing 2 housing electronic temperature monitoring equipment and a probe 3 projecting downwardly from the casing 2 for insertion into brake fluid contained in a fluid reservoir as schematically illustrated at 4 and located, for example, in the engine compartment of a motor vehicle. The probe 3 houses a heating element 5 for heating brake fluid while a temperature sensing head 6 of a thermocouple (serving as a mechanical electronic transducer) in the probe feeds heated fluid temperature information to the temperature monitoring equipment in the casing 2.

Referring especially to FIGS. 2 to 5, the probe 3 comprises an outer tubular sheath 7 defining a shroud while the heating element/thermocouple pack is carried by a spaced pair of heat-proof insulator members 8, 9 which in the probe assembled condition bear against the inner wall of the outer sheath 7, and the sheath 7 includes a cap 7B at its upper end which also serves to support the pack. The sheath 7 has a bottom closure wall 7A including a series of fluid apertures 10 (see FIGS. 4A/4B), and a separate inner tubular casing or sheath 11 is located on a stepped portion 8A of the insulator member 8, the casing 11 having an open bottom which rests on the bottom wall 7A of the sheath 7. The apertures 10 may take the form of slots (FIG. 4A) or a series of holes (FIG. 4B). An annular fluid space is present between the sheaths 7, 11, the sheaths 7, 11 can be made of suitable material such as stainless steel. A sealing ring 12 (e.g. of Tufnol (TM)) is housed in the casing 11 and the zone in the casing 11 below this ring 12 defines a housing 11A wherein a portion of fluid to be tested is semi-encapsulated or entrapped, the heating element 5 and the temperature sensing probe 6 being located in this housing 11A. In particular, the heating element 5 is located in the lower half of the housing 11A, and the probe 6 extends into the heart of the element. Initial filling of the housing 11A with fluid is achieved via the apertures 10 and 13. In FIG. 4B, the outer holes 10 are preferably aligned with the space between the shrouds 7, 11. Further, the casing 11 includes an annular series of apertures 13 adjacent to the sealing ring 12 whereby fluid can flow between the housing 11A and the annular fluid space between the sheaths 7, 11.

The leads 14A/B and 15A/B for the heating element 5 and thermocouple head 6 respectively extend up through the probe 3. The outer sheath 7 includes a level mark L (FIG. 1) to which the probe 3 should be immersed to ensure that the heating element 5 is satisfactorily immersed. Vent holes 16 are provided on the sheath 7.

Figure 6:
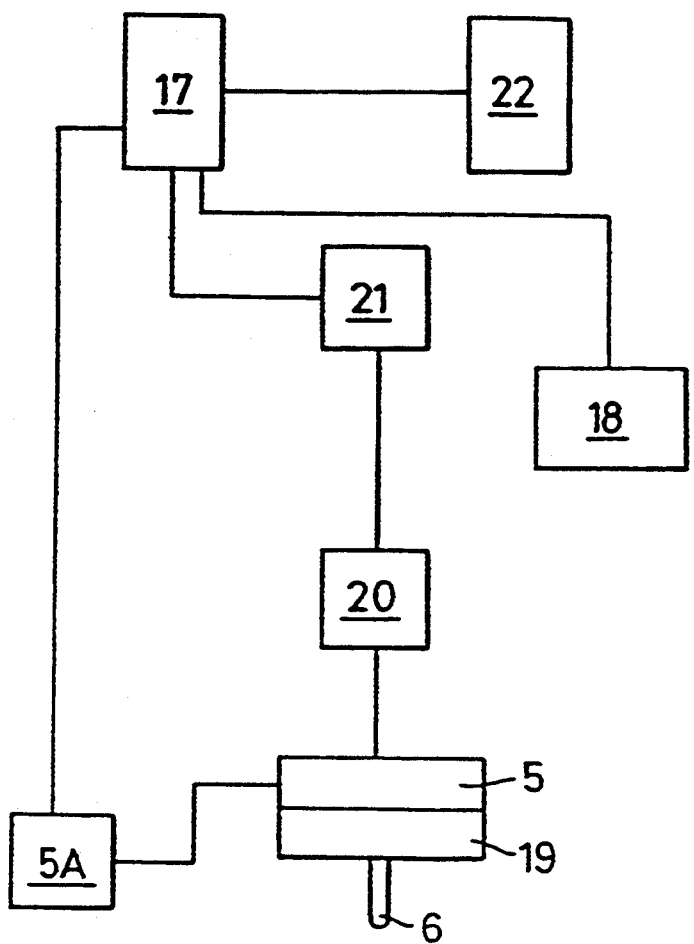
FIG. 6 shows in basic block form the electronic circuit arrangement of the fluid temperature monitoring means of the meter.

A suitable circuit for the electronic temperature monitoring equipment is shown in FIG. 6. The major item in this circuit is a micro-processor 17 which transmits each monitored temperature value in digital form to a digital display 18 (liquid crystal form). More particularly, a temperature sensing thermocouple 19 of the probe 6 is connected to a closely coupled amplifier and micro-powered thermocouple cold junction compensation chip 20, to obtain most satisfactory results. To convert the output of the matched chips into a form which the micro-processor 17 understands the output from item 20 is fed to an analogue to digital converter 21 (say 10 bit). The processor 17 is driven by an erasable programmable memory (EPROM) 22 and constantly measures and monitors the temperature of the fluid within the housing 11A. The eprom 22 holds the temperature measurement information (program) which is used in sensing the precise boiling point of the fluid and also to generate to BCD (binary coded decimal) code for the display 18. A suitable latch can be present between the EPROM 22 and the processor 17. The processor 17 serves to produce all the information for the various items of the monitoring circuit equipment. Once the equipment senses the fluid boiling point the display 18 will indicate the appropriate temperature value. Additionally, a temperature control switch 5A for the heater 5 receives signals from the microprocessor 17 to halt power to the heater when the measured fluid temperature rises to a predetermined level.

Power for the meter 1 can be taken from the vehicle battery via flexible leads 24 and terminal clips 25 and/or the meter 1 can carry its own battery (e.g. 12 volts) for example located in housing 26. The casing 2 carries on-off buttons 27, 28 for the power supply to the heating element 5 and to the display equipment respectively, while indicator lamps 29, 30 indicate when the appropriate power via button switches 27, 28 is on, although a single indicator lamp could suffice for both functions.

All the parts of the meter are housed in the casing 2 or in the probe 3 and the meter is a conveniently portable hand-held device.

In operation of the meter 1 to test the quality of brake fluid in a vehicle, the cap of the fluid reservoir housing the brake fluid to be tested is removed and the probe 3 is inserted into the fluid to the level indicated L. Brake fluid flows via the apertures 10, 13 to immerse the heating element 5 and such that a semi-encapsulated body of fluid is located in the housing 11A. Button 27 is now pressed to heat element 5 and consequently cause heating of the encapsulated brake fluid in the housing 11A. With button 28 actuated, the temperature monitoring equipment will monitor the increasing fluid temperature values.

Figure 7:
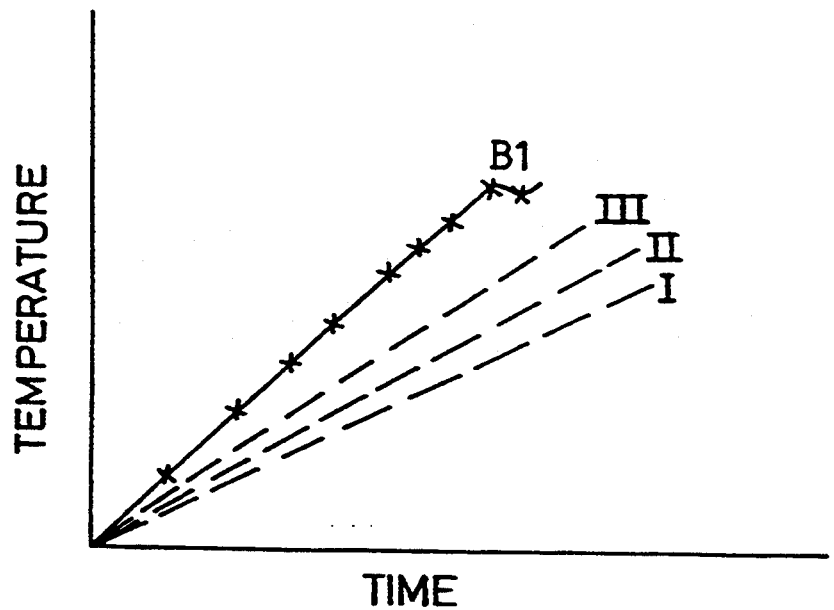
FIG. 7 shows a typical graph of temperature against time for the temperature of heated brake fluid measured by the meter.

The temperature reading rises to a first maximum or peak (B1 in the graph in FIG. 7) then falls slightly before rising again, and subsequently the temperature/time graph will have an oscillating characteristic. The reason for this feature is believed to be due to the fact that, whereas prior to the boiling point the encapsulated fluid in the housing 11A is in a substantially static state, at the on-set of boiling fluid flow paths of a reflux nature are established within the housing 11A, encouraged by the constricted nature of the fluid in the housing and by the location of the heating element 5. During this fluid movement some fluid is discharged via the apertures 10 and 13, although the apertures restrict direct flow of fluid from the housing and the fluid flow paths at boiling will generally be as indicated by the arrows at the bottom end of the probe 3 in FIG. 3. The reflex fluid flow results in instantaneous cooling at the temperature sensing zone of the probe 6 causing the temperature reading fall subsequent to the first temperature peak (B1). The highest temperature reached prior to the first temperature drop is taken as the fluid boiling point temperature —in essence this represents the equilibrium reflux boiling point temperature of the fluid. Thus the continuous graph line in FIG. 7 is produced from continuous readings from the thermocouple 6 and as will be noted at point B1 there is a temperature drop: point B1 therefore represents the fluid boiling point. The monitoring equipment will have the facility to set the value B1 for reference. Also, it is possible for the monitoring equipment to be arranged so as to equate the measured boiling point as tested to any standard required e.g. as represented by the dashed lines I, II, etc in FIG. 6. Further, ambient temperature can be automatically compensated for and batch tests can be carried out without waiting for cooling. The complete test from start to finish can be carried out very quickly and very conveniently (without the creation of mess or fumes) and, furthermore, other than the brake fluid reservoir cap, nothing has to be removed from the vehicle. The test using the meter 1 should give a tested boiling point reading very close to the correct value i.e. within 2 or 3 degree centigrade.

At a predetermined elevated temperature the switch 5A is actuated by the micro-processor 17 to halt the supply of electrical power to the heating element 5 thereby avoiding or minimising the risk of formation of noxious brake fluid vapours. The heating element 5 can provide intense local heating in the housing 11A so enabling very rapid testing of the fluid, and this is condusive to the achievement of accurate results. Also, the meter can be used satisfactorily to test liquids where normally there would be the risk of decomposition of the liquid.

Modifications are of course possible. For example a downwardly projecting shroud (indicated by dashed line 35 in FIG. 3) could be provided and this would have the advantage of "holding" the external fluid portion adjacent to the slots (apertures) 10 so enabling satisfactory testing even when the probe 3 is moved about in a reservoir of fluid to be tested.

Whereas the meter 1 was described above for testing brake fluid the meter could be used for testing other fluids, especially hydraulic fluids. In particular, transformer fluid could be tested.

I claim:

1. An apparatus for use in indicating the boiling point of fluid, especially a hygroscopic fluid such as hydraulic fluid, said apparatus comprising a meter having a portable handheld type probe portion for insertion into a body of fluid in a fluid reservoir for in situ testing of fluid in the fluid reservoir, heating means disposed in said probe portion for heating fluid in which the probe portion is disposed, and temperature monitoring means for monitoring a rise in the temperature of fluid heated by said heating means for use in determining the boiling point of the fluid; wherein said probe portion comprises a casing in which a substantially enclosed chamber is provided at a lower end of the probe the holding a portion of said body of fluid, said heating means and a temperature sensor of said monitoring means being disposed in said chamber; wherein said chamber is sufficiently enclosed at all sides as to cause fluid in the chamber to be in a substantially static state prior to the on-set of boiling of the fluid and to produce reflux-type fluid flow paths within the chamber once boiling of the fluid has commenced, port means being provided in a peripheral wall of said casing in proximity to an upper end of the chamber and at a lower end of the probe portion for allowing only limited flow to and from said chamber.

2. An apparatus as claimed in claim 1, wherein an outer shroud is provided surrounding the casing, an outer compartment for holding fluid being defined between the casing and the outer shroud.

3. An apparatus as claimed in claim 2, wherein said fluid port means comprises a first fluid aperture means at the lower end of the probe portion, and a second fluid aperture means in the peripheral wall of the casing, said second fluid aperture means communicating said chamber with outer compartment.

4. An apparatus as claimed in claim 3, wherein said outer shroud has a transverse bottom wall in which said first fluid aperture means is provided; and wherein said casing has an open lower end which rests on said bottom wall with said first fluid aperture means underlying said chamber.

5. An apparatus as claimed in claim 4, wherein said second fluid aperture means is disposed above the temperature sensor of said temperature monitoring means.

6. An apparatus as claimed in claim 1, wherein said monitoring means comprises electronic devices.

7. An apparatus as claimed in claim 6, wherein said electronic devices comprise a microprocessor housed in said meter.

8. An apparatus as claimed in claim 1, wherein the temperature sensor of said temperature monitoring means comprises a thermocouple sensor.

9. An apparatus as claimed in claim 8, wherein said thermocouple sensor is electrically connected to a compensation chip and an amplifier for delivering an analog output signal thereto; wherein said compensation chip and amplifier are electrically connected to an analog/digital convertor for delivering the output signal thereto in compensated and amplified form; and wherein said analog/digital convertor is electrically connected to the microprocessor for providing the output signal thereto in digital form.

10. An apparatus as claimed in claim 9, wherein a digital display is connected to the microprocessor for displaying fluid temperatures measured by said thermocouple sensor.

11. An apparatus as claimed in claim 7, wherein microprocessor is electrically connected to a programmable memory.

12. An apparatus as claimed in claim 6, wherein said meter houses an electrical battery for supplying electrical power to the heating means and to the temperature monitoring means.

13. An apparatus as claimed in claim 6, wherein an electrical cable and connector means are provided for supplying electrical power from a vehicle battery to said meter.

14. An apparatus as claimed in claim 1, wherein said probe portion is provided with at least one ventilation aperture.

15. An apparatus as claimed in claim 1, wherein said probe portion is provided with a level indicator means for indicating when the probe portion has been inserted into the body of fluid to a depth sufficient to completely submerge said chamber below the surface of the body of fluid.

16. An apparatus as claimed in claim 1, wherein the heating means is provided with a control means for automatically disconnecting the heating means from a power source therefor when the portion of the body of fluid in said chamber reaches a predetermined temperature.

17. An apparatus as claimed in claim 1, wherein said heating means comprises a heating element located in a lower zone of the chamber, said heating element having an annular form with a central space; and wherein the sensor of the temperature monitoring means extends into said central space of the heating element.

18. An apparatus as claimed in claim 1, wherein said casing comprises a tube, a seal member being disposed in said tube and defining an upper end of said chamber.

19. An apparatus as claimed in claim 1, wherein said fluid port means comprises a plurality of individual apertures.

20. An apparatus as claimed in claim 2, wherein said outer shroud has a bottom wall which extends under the chamber as a bottom wall thereof.

21. An apparatus as claimed in claim 1, wherein said chamber is substantially free of internal obstructions for permitting the fluid in the chamber to substantially freely circulate around the heating means and the temperature monitoring means.

22. A method of determining the boiling point of a fluid, especially a hygroscopic fluid such as hydraulic fluid, comprising the steps of:
providing an apparatus according to claim 1; hand-holding the meter of said apparatus and inserting the probe portion thereof substantially vertically into a body of fluid in a reservoir to a level substantially completely immersing the heating means and the sensor of the temperature monitoring means in the portion of the body of fluid in the chamber; heating the portion of the body of fluid in the chamber with said heating means; and monitoring the temperature of the portion of the body of fluid in the chamber with said monitoring means and recording a maximum temperature reached.

23. An apparatus as claimed in claim 1, wherein is provided an insulated spacer means engaging an internal wall of the probe portion, said spacer means serving to locate leads of the heating means, and of the temperature monitoring means.

* * * * *